US012578267B2

(12) United States Patent
Kosenka et al.

(10) Patent No.: US 12,578,267 B2
(45) Date of Patent: Mar. 17, 2026

(54) CARBON MEASUREMENTS IN AQUEOUS SAMPLES USING OXIDATION AT ELEVATED TEMPERATURES AND PRESSURES CREATED BY RESISTIVE HEATING

(71) Applicant: BL TECHNOLOGIES, INC., Minnetonka, MN (US)

(72) Inventors: Paul P. Kosenka, Denver, CO (US); Paulus J. Vanhoudt, Erie, CO (US)

(73) Assignee: BL TECHNOLOGIES, INC., Minnetonka, MN (US)

( * ) Notice: Subject to any disclaimer, the term of this patent is extended or adjusted under 35 U.S.C. 154(b) by 948 days.

(21) Appl. No.: 17/784,602

(22) PCT Filed: Dec. 11, 2019

(86) PCT No.: PCT/US2019/065626
§ 371 (c)(1),
(2) Date: Jun. 10, 2022

(87) PCT Pub. No.: WO2021/118550
PCT Pub. Date: Jun. 17, 2021

(65) Prior Publication Data
US 2023/0012945 A1     Jan. 19, 2023

(51) Int. Cl.
*G01N 21/3504*     (2014.01)
*B01L 3/00*     (2006.01)
(Continued)

(52) U.S. Cl.
CPC .... *G01N 21/3504* (2013.01); *B01L 3/502715* (2013.01); *G01N 1/42* (2013.01);
(Continued)

(58) Field of Classification Search
CPC ........ G01N 21/3504; G01N 1/42; G01N 1/44; G01N 33/004; G01N 33/1846;
(Continued)

(56) References Cited

U.S. PATENT DOCUMENTS 8,101,417 B2     1/2012   Conway et al.
8,101,418 B2     1/2012   Conway et al.
(Continued)

FOREIGN PATENT DOCUMENTS

CN       101796393 A     8/2010
DE        19955150 A1     6/2001
(Continued)

OTHER PUBLICATIONS

Chinese Patent Office, The Second Office Action issued in CN Application No. 201980103550.7 on Jan. 25, 2025, 13 pages.
(Continued)

*Primary Examiner* — Xiuyu Tai
(74) *Attorney, Agent, or Firm* — Meunier Carlin & Curfman LLC

(57) ABSTRACT

Apparatus and methods for measuring the concentrations of organic and inorganic carbon, or of other materials in aqueous samples are described, having a reactor that is resistively heated by passing an electric current through the reactor.

14 Claims, 14 Drawing Sheets

(51) Int. Cl.
    *G01N 1/42*     (2006.01)
    *G01N 1/44*     (2006.01)
    *G01N 33/00*     (2006.01)

(52) U.S. Cl.
    CPC ............. *G01N 1/44* (2013.01); *G01N 33/004*
    (2013.01); *B01L 2300/0663* (2013.01); *B01L*
    *2300/1833* (2013.01); *B01L 2300/1894*
    (2013.01); *B01L 2400/0633* (2013.01)

(58) Field of Classification Search
    CPC .............. G01N 31/12; B01L 3/502715; B01L
    2300/0663; B01L 2300/1833; B01L
    2300/1894; B01L 2400/0633; B01L
    3/0268; B01L 7/52; B01L 3/5088; B01L
    2300/0819; B01L 2300/185; B01L
    2300/1838; B01L 2300/1827; Y10T
    436/17; Y10T 137/87652; Y10T 436/18;
    Y10T 137/87249; Y10T 436/23; Y10T
    436/235; Y10T 137/87161; Y10T
    436/204998; Y10T 436/2575; Y10T
    436/11; Y10T 137/8593; Y02A 20/20;
    B25J 9/026; C12Q 1/686
    See application file for complete search history.

(56) References Cited

U.S. PATENT DOCUMENTS

| | | |
|---|---|---|
| 8,101,419 B2 | 1/2012 | Conway et al. |
| 8,101,420 B2 | 1/2012 | Conway et al. |
| 2008/0038163 A1 | 2/2008 | Boege et al. |
| 2011/0155912 A1 | 6/2011 | Conway et al. |
| 2018/0229230 A1* | 8/2018 | Chung .................. B01L 3/0268 |

FOREIGN PATENT DOCUMENTS

| | | |
|---|---|---|
| JP | 2010538297 A | 12/2010 |
| WO | 200042293 A1 | 7/2000 |
| WO | 2000042293 A1 | 7/2000 |
| WO | 2009032205 A2 | 3/2009 |

OTHER PUBLICATIONS

Indian Patent Office, First Examination Report issued in IN Application No. 202247038323 on Jan. 29, 2025, 5 pages.
Japanese Patent Application No. 2022-535925, Notice of Reasons for Refusal dated Sep. 5, 2023, 6 pages.
Chinese Patent Office, The First Office Action issued in CN Application No. 201980103550.7 on Mar. 29, 2024, 12 pages.
International Search Report and Written Opinion, in connection with International Application No. PCT/US2019/065626, dated Oct. 1, 2020.
Rydfjord, J., Svensson, F., Fagrell, M., Savmarker, J., Thulin, M., & Larhed, M. (2013). Temperature measurements with two different IR sensors in a continuous-flow microwave heated system. Beilstein journal of organic chemistry, 9, 2079-2087. https://doi.org/10.3762/bjoc.9.244.

* cited by examiner

1

CARBON MEASUREMENTS IN AQUEOUS SAMPLES USING OXIDATION AT ELEVATED TEMPERATURES AND PRESSURES CREATED BY RESISTIVE HEATING

CROSS REFERENCE TO RELATED APPLICATIONS

This application is a United States National Phase Patent Application of International Patent Application Number PCT/US2019/065626, filed on Dec. 11, 2019, which is incorporated by reference herein in its entirety.

FIELD

The embodiments described herein generally relate to methods and apparatus for making very precise, reliable and reproducible measurements of concentrations of organic, inorganic and total carbon present in aqueous samples. Such methods and apparatus may be used, for example, to determine the concentration of total organic carbon (TOC) in drinking water, raw water, wastewater, industrial process streams and the like. Such measurement may be utilized for various important commercial purposes, for example to optimize water purification processes, to detect spills, and to monitor compliance with environmental regulations. The methods and apparatus described herein can generally be applied both to measuring discrete aqueous samples, such as those encountered in a laboratory environment, and to monitoring flowing streams to provide real-time concentration data.

BACKGROUND

Total organic carbon is a well-established water quality parameter that quantifies the overall concentration of organic substances, all of which are typically regarded as contaminants, in an aqueous environment. Total organic carbon in an aqueous sample may be composed of either one or two components-dissolved organic carbon (DOC) and particulate organic carbon. The measurement of DOC is conventionally accomplished by filtering the water sample, commonly through a 0.45-$\mu$m filter, to remove particulate organic carbon prior to performing an analysis for DOC. The limitations of conventional apparatus and techniques for Such analysis often lead to the result that only DOC is effectively measured, instead of TOC, because the particulates in a sample containing both forms of organic carbon typically cause errors in the measurement and plug fluid passages causing hardware failures.

In the following description, DOC is used to refer to measurements in which the sample has first been filtered to remove particulates, while TOC is used herein to refer to measurements in which the sample has not been filtered. In other respects, however, the following description is relevant to both DOC and TOC measurements.

In one known approach DOC and/or TOC, the organic compounds in an aqueous sample are oxidized to carbon dioxide ($CO_2$) and the $CO_2$ in the sample is then measured. In addition to organic carbon components, the water sample may initially contain $CO_2$ and other inorganic forms of carbon (e.g., in the form of bicarbonate and carbonate salts). Together, these forms of inorganic carbon are referred to herein as IC. Total carbon (TC) concentration in an aqueous sample is therefore the sum of the TOC and IC concentrations.

The measurement of total organic carbon in a sample relies on the conversion of organic carbon to carbon dioxide. The more common methods have been high temperature combustion, vaporizing the sample and heating the gas to over 600° C. Air or oxygen is used to react with the organics at high temperature to accomplish the conversion of organic carbon to carbon dioxide. The other common method has been to mix the liquid sample an oxidizing agent such as persulfate and then activate the persulfate with heat or ultraviolet radiation. The activated persulfate will convert the organic carbon to carbon dioxide. After conversion the carbon dioxide is measured and the amount of organic carbon is calculated based on the amount of carbon dioxide measured.

Both these methods have drawbacks. Samples containing high salt concentrations such as sodium chloride in brine will cause maintenance issues with combustion techniques. Salt will deposit in high temperature furnace of combustion instruments. If these samples are repeatedly introduced to the furnace it will eventually clog and have to be cleaned. The persulfate method also suffers when high salt solutions are analyzed. The chloride is converted by the oxidizing agent to chlorine placing a high demand for the addition of oxidizer to the sample.

Furthermore, conventional measurement apparatus using high-temperature combustion trap a water sample in a reactor along with a small amount of air and oxidizing agent. A heater on the outside of the reactor heats the reactor (and sample) to the required temperature. However, the current configuration of the reactor has drawbacks. The time it takes to heat the reactor to temperature is slow and not uniform. The heater is not in contact with the reactor so the heater heats up the air around the heater and also transfers heat due to radiation. The heater is not in contact with the reactor so that after the reaction occurs it needs to be cooled down quickly to prepare for the next sample. The other drawback is that installing a temperature measuring device on the reactor may cause local heat transfer to be altered in the region where the device is attached.

These and other limitations of, and deficiencies in, the prior art approaches to IC, TOC and TC measurements are over come in whole, or at least in part, by the methods and apparatus of the described embodiments.

SUMMARY

By contrast with the limitations of the prior approaches to making such carbon concentration determinations in aqueous samples, as discussed above, the methods and apparatus described herein are capable of measuring all of the aforementioned parameters in samples that contain concentrations of TOC, dissolved solids, and particulates. In general a sample is drawn into the analyzer described herein, reagents are added, and the sample is diluted as necessary, and then the sample enters the oxidation reactor where super critical water oxidation is used to effect the conversion of organic carbon to carbon dioxide. The critical point of water is 374° C. and 3200 psia. To reach these temperatures and pressures the water sample is trapped in the reactor with a small amount of air and oxidizing agent. Because it is a closed system the pressure inside the tube reaches the critical point. Under these conditions organics as well as organic particles are converted to carbon dioxide.

Described herein are embodiments of a measurement apparatus and a method of sample heating wherein the reactor is resistively heated by passing electrical current directly through a tube of the reactor and measuring the temperature of the reactor using non-contact devices such as an IR sensor. Having the reactor reach the critical temperature faster allows for shorter throughput time of measurement and quicker results. While some conventional measurement apparatus take approximately 120 seconds to reach temperature, the use of resistive heating as described herein takes approximately 18 seconds. It also allows for less overshoot and a tighter temperature accuracy.

In one aspect, the present disclosure relates to an apparatus for treating a liquid sample containing organic material. In one embodiment, the device includes: (a) a reactor having reactor inlet and reactor outlet ports and a reactor interior for containing a liquid sample under above-ambient temperature and pressure conditions; (b) high pressure fluid reactor valve members at said reactor inlet and reactor outlet ports, said reactor valve members allowing fluid flow respectively into or out of the reactor interior when in an open-valve mode or, alternatively, capable of sealing the reactor interior when in a closed-valve mode; (c) a reactor heating system including an electrical current source operably connected to the reactor, the electrical current source configured to pass an electrical current through the reactor to rapidly and cyclically heat the reactor interior and a liquid sample sealed in the reactor interior to a temperature of about 150° C. to 650° C. or higher, while the reactor interior and the reactor valve members maintain the sample under sealed conditions; and, (d) a reactor cooling system adapted for rapidly and cyclically cooling the reactor interior and a reactor product sealed in the reactor interior following a heating cycle.

In one embodiment, a sensor is configured to determine a temperature value of the reactor.

In one embodiment, the sensor is configured to measure electromagnetic radiation.

In one embodiment, the sensor is configured to measure infrared radiation.

In one embodiment, the sensor is operably connected to the reactor heating system.

In one embodiment, the sensor is operably connected to the reactor cooling system.

In one embodiment, the reactor is comprised of titanium and its alloys, tantalum, Inconel 625, Hastelloy C-276, or combinations thereof.

In another aspect, the present disclosure relates to a method for treating a liquid sample containing organic material utilizing a liquid sample treatment apparatus. In one embodiment, the method includes: (a) providing a liquid sample treatment apparatus comprising the following features: (i) a reactor having reactor inlet and reactor outlet ports and a reactor interior for containing a liquid sample under above-ambient temperature and pressure conditions; (ii) high-pressure fluid reactor valve members at said reactor inlet and reactor outlet ports, said reactor valve members allowing fluid flow respectively into or out of the reactor interior when in an open-valve mode or, alternatively, capable of sealing the reactor interior when in a closed-valve mode; (iii) a reactor heating system comprising an electrical current source operably connected to the reactor, the electrical current source configured to pass an electrical current through the reactor to rapidly and cyclically heat the reactor interior and a liquid sample sealed in the reactor interior to a temperature of about 150° C. to 650° C. or higher, while the reactor interior and the reactor valve members maintain the sample under sealed conditions; and, (iv) a reactor cooling system adapted for rapidly and cyclically cooling the reactor interior and a reactor product sealed in the reactor interior following a heating cycle; (b) mixing a known volume of the sample with one or more other liquids selected from oxidizer, acid and dilution water to form a sample mixture; (c) flowing at least a portion of the sample mixture into the interior of the reactor, said reactor being adapted to be alternately and repeatedly opened and sealed at the reactor inlet and reactor outlet ports; (d) sealing the portion of sample mixture in the interior of the reactor by closing the valve members at the reactor inlet and reactor outlet ports; (e) passing an electrical current through the reactor for a time sufficient substantially to oxidize the organic material and form the reactor product; (f) stopping the heating step and then rapidly cooling the interior of the reactor and the reactor product inside to substantially ambient conditions to form cooled liquid and gaseous reactor products; and, (g) opening the reactor and removing the cooled liquid and gaseous reactor products form the reactor interior.

In one embodiment, the interior of the reactor and the sample portion inside is rapidly heated to a temperature between 150° C. to about 650° C.

In one embodiment, a sensor is provided, the sensor configured to measure a temperature value of the reactor.

In one embodiment, the sensor is configured to measure electromagnetic radiation.

In one embodiment, the sensor is configured to measure infrared radiation.

In one embodiment, a signal generated by the sensor is used to decide when to stop the heating step.

In one embodiment, the reactor is comprised of titanium and its alloys, tantalum, Inconel 625, Hastelloy C-276, or combinations thereof.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The accompanying drawings, which are incorporated in and constitute a part of this specification, illustrate embodiments and together with the description, serve to explain the principles of the methods and systems.

DETAILED DESCRIPTION

Figure 1:
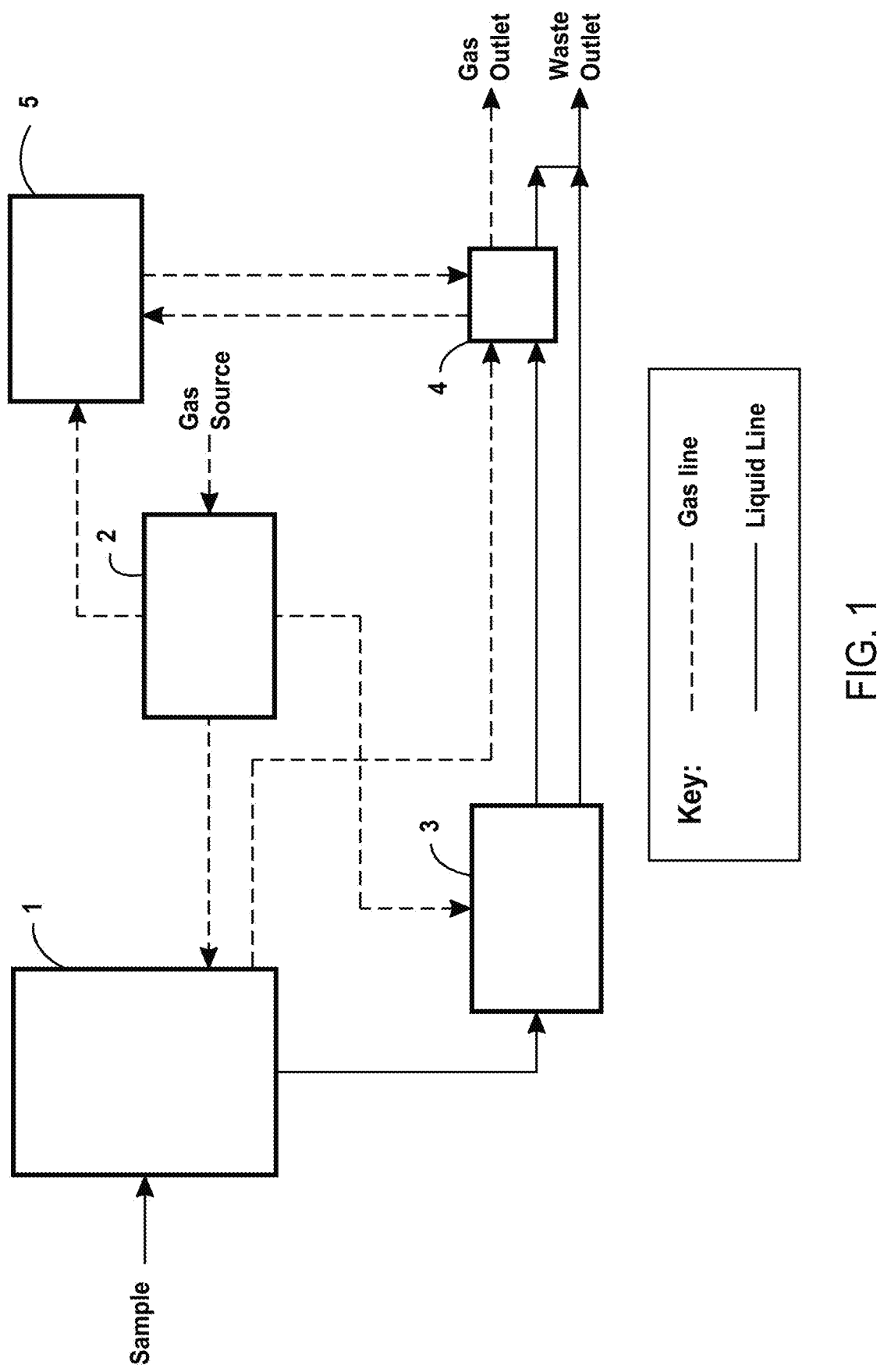
FIG. 1 (Block Diagram) is a diagram showing in block form the five key fluidic sub-assemblies of an embodiment of a measurement apparatus.

FIG. 1 is a block schematic of one embodiment of an automated carbon measurement apparatus/analyzer illustrating five component sub-assemblies 1 to 5 that comprise the analyzer. As illustrated in FIG. 1, an aqueous sample is drawn into a sample handling sub-assembly 1 of the apparatus, where the desired volumes of acid reagent and/or oxidizer reagent are added to a selected volume of sample. The sample may also be diluted at this stage with low-TOC dilution water if necessary before being passed to reactor sub-assembly 3. Additional details about the shown and described measurement apparatus/analyzer can be found in U.S. Pat. Nos. 8,101,417; 8,101,418; 8,101,419; and 8,101,420, each of which are fully incorporated by reference and made a part hereof. The sample, reagents and dilution water if any are mixed in the sample-handling portions of the apparatus to create a sample mixture comprising a substantially homogenous solution or suspension. If NPOC is to be measured, the acidified sample mixture also is sparged with $CO_2$-free gas provided by the gas control sub-assembly/module 2. The flow rate of the sparge gas is controlled to ensure that IC in the sample is removed efficiently and substantially completely. If TC or IC is to be measured, the sample mixture is mixed but not sparged.

A portion of the homogenous solution/suspension is then transferred to the reactor sub-assembly 3. If NPOC or TC is to be measured, the solution/suspension containing oxidizer is heated in a sealed reactor to oxidize the organic compounds in the solution/suspension, and then it is cooled to near room temperature. If IC is to be measured, oxidizer is not added to the solution/suspension. In this case, the solution/suspension may be warmed to facilitate conversion of bicarbonates and carbonates to $CO_2$, but it is not heated so much that oxidation of organic compounds occurs.

Next, a stream of carrier gas from the gas control assembly/module 2 transfers the liquid and gas products in the reactor sub-assembly 3 to a gas/liquid separator sub-assembly/module 4. The liquid exits the analyzer from the gas/liquid separator module 4 while the gas product, containing the $CO_2$, flows to the NDIR detector sub-assembly 5. After the $CO_2$, in the gas product is measured, the gas product and carrier gas mixture can be flowed through the gas/liquid separator module 4, and vented to the atmosphere.

Figure 2:
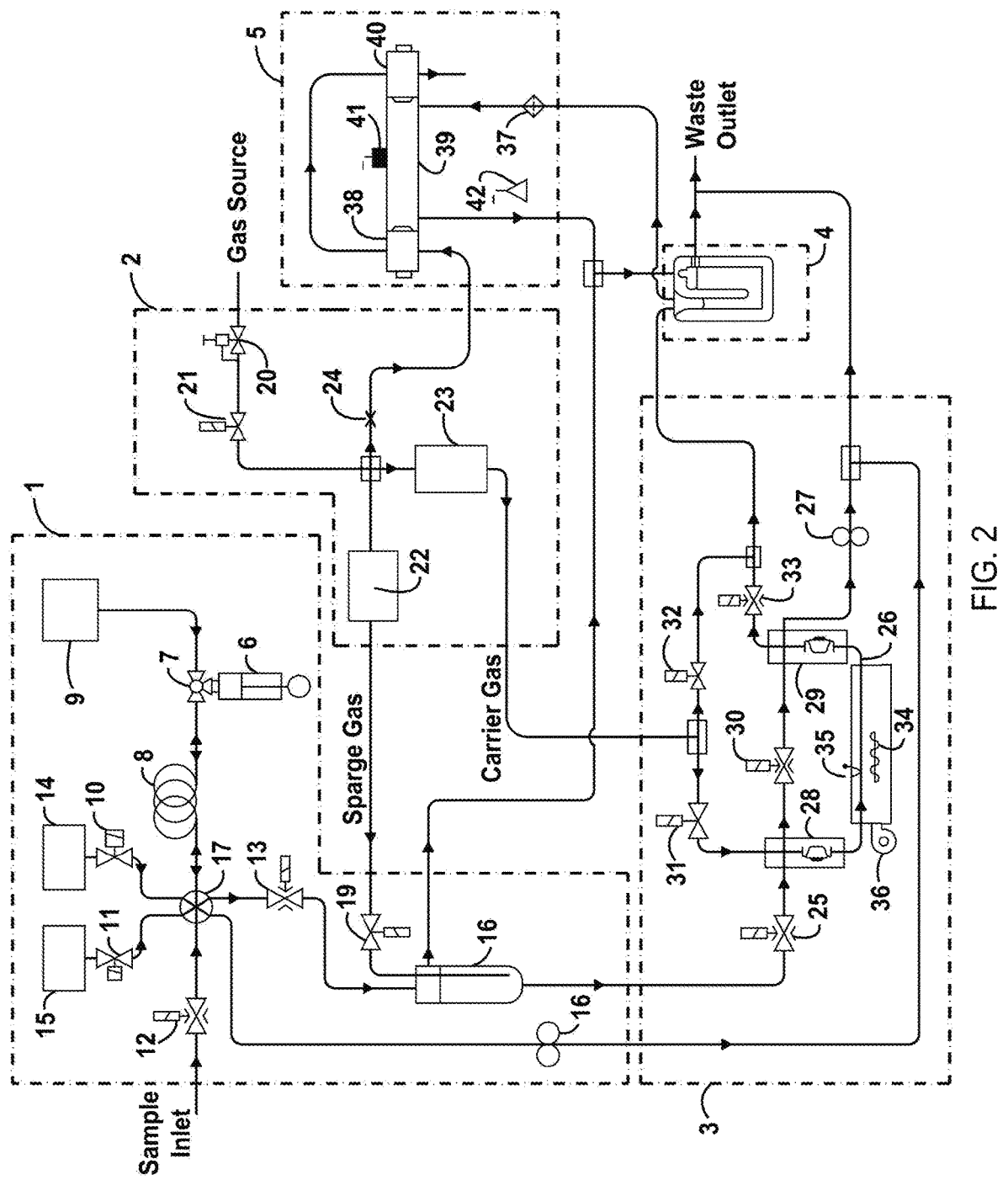
FIG. 2 (Fluidics Schematic) is an overall schematic of the functional components of a measurement apparatus showing in detail the several component elements that comprise each of the several fluidic sub-assemblies as illustrated in FIG. 1.

FIG. 2 is a schematic showing the several fluidic components of an embodiment of the apparatus in more detail. In FIG. 2, sub-assemblies 1 to 5 as shown in FIG. 1 are delineated by broken lines. The sample-handling sub-assembly 1 comprises a syringe 6 that is connected through a three-way valve 7 to a coil of tubing 8 and a dilution water reservoir 9 containing low-TOC dilution water. A representative practice using the apparatus as illustrated in FIG. 2 is described below. It will be understood, however, that alternative sequences and methods for introducing the sample, reagent(s) and dilution water into the system could be used consistent with the scope of this invention. For example, using the apparatus illustrated in FIG. 2, the oxidizer and acid reagents could be moved from coil 8 to a mixing location in the apparatus, such as to mixer/sparger 18, prior to introducing the sample into the system in order to maintain a separation between these components until they are ready to be mixed at the mixing location.

Initially, the syringe is empty, and the valve 7 and coil 8 contain only dilution water. The volume of coil 8 is designed and selected to be at least as large as, and preferably larger than, the volume of syringe 6, so the only liquid that can enter the syringe is dilution water from coil 8 or reservoir 9. When an analysis begins, valve 10 is open, and valves 11, 12, and 13 are closed. Syringe 6 starts filling with dilution water drawn from a syringe end of coil 8, which causes oxidizer reagent from oxidizer reagent reservoir 14 to be drawn through the six-way fluid element 17 and into a sample/reagent end of coil 8. When syringe 6 has drawn the required volume of oxidizer into the sample/reagent end of coil 8, Syringe 6 stops momentarily and valve 10 closes. Valve 11 opens and syringe 6 draws additional dilution water from the y syringe end of coil 8 into syringe 6, which in turn draws the required volume of acid from acid reservoir 15 into the sample/reagent end of coil 8, where it may partially mix with the oxidizer reagent already in this end of coil 8. When the desired volume of acid has entered coil 8, the syringe 6 stops momentarily, valve 11 closes, and valve 12 opens to allow the required volume of sample to be drawn into the sample/reagent end of coil 8, as additional dilution water from the syringe end of coil 8 is drawn into syringe 6. When the required volume of sample has entered the coil, syringe 6 stops again, and valve 12 closes. The coil 8 now contains the desired volumes of oxidizer, acid, and sample solution required for the measurement. Coil 8 may or may not contain a material amount of dilution water at this point, depending on the internal volume of coil 8 relative to the volumes of oxidizer, acid and sample drawn into coil 8, and also depending upon whether or not the sample requires dilution prior to analysis.

It will be understood that, if the procedure described above took any significant amount of time to complete, there would be an opportunity for oxidizer reagent or, perhaps, even acid, from the sample/reagent end of coil 8 to diffuse into dilution water at the syringe end of coil 8, which could lead to contamination of the syringe. In practice, however, the several steps of filling coil 8 are completed in a sufficiently short time that there is no opportunity for reagents drawn into the sample/reagent end of coil 8 to diffuse into the dilution water at the syringe end of coil 8.

In some cases, the source of the sample is a long distance from the analyzer, especially when embodiments of the analyzer described herein is used to monitor a process stream of an industrial operation. In such a situation, the analyzer may not provide real-time measurements if the only way of pumping the sample to the analyzer were the syringe pump. Therefore, in one of the embodiments described herein, the apparatus also includes a pump 16 which can rapidly draw a fresh portion of sample to the six-way union 17. Once the new sample portion has been delivered to element 17, it can be drawn into coil 8 quickly by further opening syringe 6 at the appropriate time.

The next step in the measurement method is to open valve 13. With valve 13 open, the step of closing syringe 6 results in moving the liquids from coil 8 to a mixing location in the system, such as to the mixer/sparger component 18, where the reagents, sample, and dilution water, if any, are thoroughly mixed. Particulate material in the sample is kept in suspension so that the solution/suspension is substantially homogeneous.

In one alternative embodiment, the acid and oxidizer are first drawn into coil 8 and then are transferred into mixing/sparging chamber 18. The sample and dilution water (if any) are then drawn into coil 8 and transferred into mixing/sparging chamber 18 where the sample, acid, oxidizer, and dilution water are mixed. Transferring the liquids to the mixing/sparging chamber 18 in two steps has the advantage of preventing premature reaction of IC in the sample with the acidic reagents in coil 8. Generation of gas in coil 8 (from reaction of IC in the sample with acid) reduces the volume of sample drawn into coil 8, adversely affecting the accuracy of the measurement.

Mixer/sparger 18 includes a mixing and sparging chamber that also is designed to provide for sparging $CO_2$-free gas through the solution/suspension to remove IC, if NPOC is to be measured. For sparging, after the chamber element of mixer/sparger 18 contains the reagents, sample and dilution water (if any), valve 19 opens to allow the sparge gas to bubble through the chamber element of mixer/sparger 18. The gas can be provided from a pressurized gas cylinder (not shown) or from a pump (not shown) that draws ambient air through an absorber that purifies the air sufficiently for use as a $CO_2$-free sparge gas, and/or as a carrier gas, and/or as a purge gas. In either case, the $CO_2$-free gas is prepared for use in gas control sub-assembly module 2. Sub-assembly 2 includes a pressure-regulating device 20 that adjusts the pressure of the gas to about 20 psig. A proportioning valve 21 controls the flow rate of the gas flowing through valve 19 by means of a sparge gas flow sensor 22. Additionally, a carrier gas flow sensor 23 in another conduit branch can be used to monitor and control the flow rate of the carrier gas to reactor sub-assembly 3. Additionally, a restrictor 24 in still another conduit branch can be used to provide for a small flow rate of purge gas to the NDIR detector.

In an alternative embodiment, a valve (not shown) can be used to direct the gas that exits the chamber element of mixer/sparger 18 through the gas/liquid separator unit 4 and then to the NDIR sub-assembly 5. This arrangement would allow the completeness of the sparging process to be monitored. Thus, the sparging is considered complete when the NDIR indicates that the concentration of $CO_2$ in the sparge gas going to the NDIR has decreased to a very small (negligible) value.

When the sparging and/or mixing in the chamber element of mixer/sparger 18 is complete, valve 25 opens to allow all or a portion of the solution/suspension in the chamber element to be drawn into the interior of reactor 26 by pump 27. High-pressure reactor inlet and outlet valves 28 and 29 respectively are open at this point. Valves 30, 31, 32, and 33 are closed. The reactor heater 34 is off, and reactor 26 is near ambient temperature. Pump 27 operates until sufficient liquid from chamber 18 has passed through the interior of reactor 26. Substantially to rinse out any remaining prior sample and to fill the reactor tube inside reactor 26. At this point, pump 27 is stopped, and valves 25, 28, and 29 close.

Reactor valves 28 and 29 allow the valve housings to be flushed after these valves are closed. The flushing step removes excess sample that contains $CO_2$ formed by the acidification of the IC in the sample. If this $CO_2$ were not flushed out of the valves, it would cause an error in the subsequent measurement. To flush the reactor valve housings, valves 30 and 31 are opened, and residual liquid and gases in these housings can then be pumped out by pump 27 and replaced by carrier gas.

After the reactor tube of reactor 26 has been filled with sample and reactor valves 28 and 29 have been flushed, valve 31 closes and valve 32 opens to allow carrier gas to flow from sub-assembly 3 through valve 32, pass through the gas/liquid separator 4, and then pass to the NDIR detector sub-assembly 5. How of carrier gas at this time is necessary to allow the NDIR detector to reach a steady baseline prior to the subsequent $CO_2$ measurement. An in-line filter 37 may be provided between gas/liquid separator 4 and the NDIR unit to prevent aerosols from the reactor 26 and/or from gas/liquid separator 4 from entering the optical path 39 of the NDIR detector.

To measure NPOC or TC, the organics contained in the sample portion in the reactor tube of reactor 26 must be oxidized. This oxidation can be made to occur by heating the interior of reactor 26 with a heater 34, and/or by resistive heating as described herein, while controlling the temperature using a temperature sensor 35. The sealed reactor can be heated, for example, to a temperature between about 150° C. and 650° C. (preferably between about 300° C. and 400° C., and between about 350° C. and 390° C. in one embodiment). The heating period may be between about one to thirty minutes, preferably between about two and four minutes, and approximately 3 minutes in one embodiment. During this period, organics are oxidized in the sample portion in the reactor. At the end of that period, heating element 34 is turned off, and fan unit 36 is turned on to blow ambient air over reactor 26, cooling it rapidly to near room temperature. Because of the small mass of reactor 26, it is typically cooled by this cooling step to near ambient temperature in less than about 90 seconds.

To measure IC, the liquid inside reactor 26 is not oxidized. The reactor is filled as described above, but reactor 26 is heated only to a temperature sufficient to facilitate formation of $CO_2$ from bicarbonates and carbonates (i.e., typically to no more than about 100° C.). The subsequent cooling step may in this case be abbreviated or omitted entirely. Furthermore, the oxidizer reagent is not required for IC measurements, and its addition to the sample prior to the reactor step can thus be omitted to reduce operating cost and make the analysis faster.

When the heating and cooling of reactor 26 is completed (or the comparable IC reactor sequence is completed), Valves 30 and 32 close, and valves 28, 29, 31, and 33 open. This apparatus configuration allows carrier gas to flow through the reactor tube of reactor 26, and carry the reactor products through gas/liquid separator 4, to the NDIR sub-assembly and along the NDIR optical path 39.

The NDIR measures the absorbance of the $CO_2$ in the gas flowing along NDIR optical path 39 at a wavelength of approximately 4.26 μm, e.g., 4.26 μm±0.2 μm. As the $CO_2$ carried from reactor 26 enters and passes through the NDIR. the absorbance measurement begins at a baseline level, rises up to and passes through a maximum level, and then returns to the baseline level that existed before the valves associated with reactor 26 opened. Either the height of the absorbance peak (or the depth of the intensity trough) or the cone-shaped area of the absorbance response curve can be calibrated and used to determine the amount of $CO_2$ contained in the gas product coming from the reactor.

Figure 6:
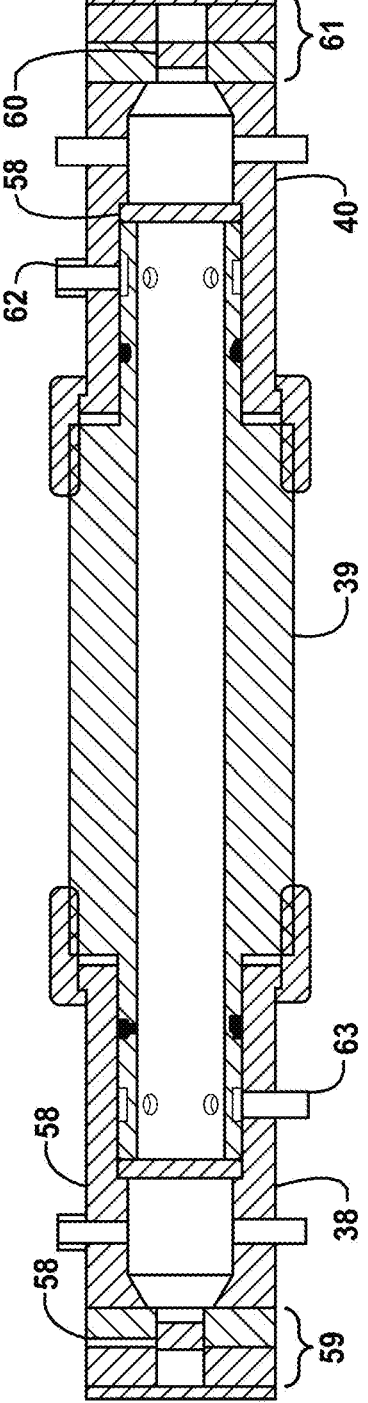
FIG. 6 (Non-Dispersive Infrared (NDIR) Optical Bench) is a schematic, partially cut-away/sectional view of an NDIR sub-assembly.

The NDIR detector is comprised of three chambers, as seen in FIGS. 2 and 6. One chamber 38 contains the IR source. The central chamber, which is the NDIR optical path 39, is the chamber through which the carrier gas and the gas product from reactor 26 (which includes the $CO_2$) flow. The third chamber 40 contains the IR detector. Chambers 38 and 40 are flushed by $CO_2$-free gas provided through the conduit that includes flow controller 24 so that $CO_2$ in the ambient air does not affect the measurements made with the NDIR. The NDIR further includes an associated temperature sensor 41 and an associated pressure sensor 42. proximately located relative to the NDIR, which monitors atmospheric pressure outside the NDIR (which is essentially the same as the pressure of the $CO_2$ in the NDIR). The temperature and pressure measurements made respectively by temperature sensor 41 and pressure sensor 42 can be used to compensate the response of the NDIR for variations in the temperature and pressure of the gas being measured. Alternatively, sensors 41 and/or 42 may be omitted if the measurement does not require temperature and/or pressure compensation.

Figure 3:
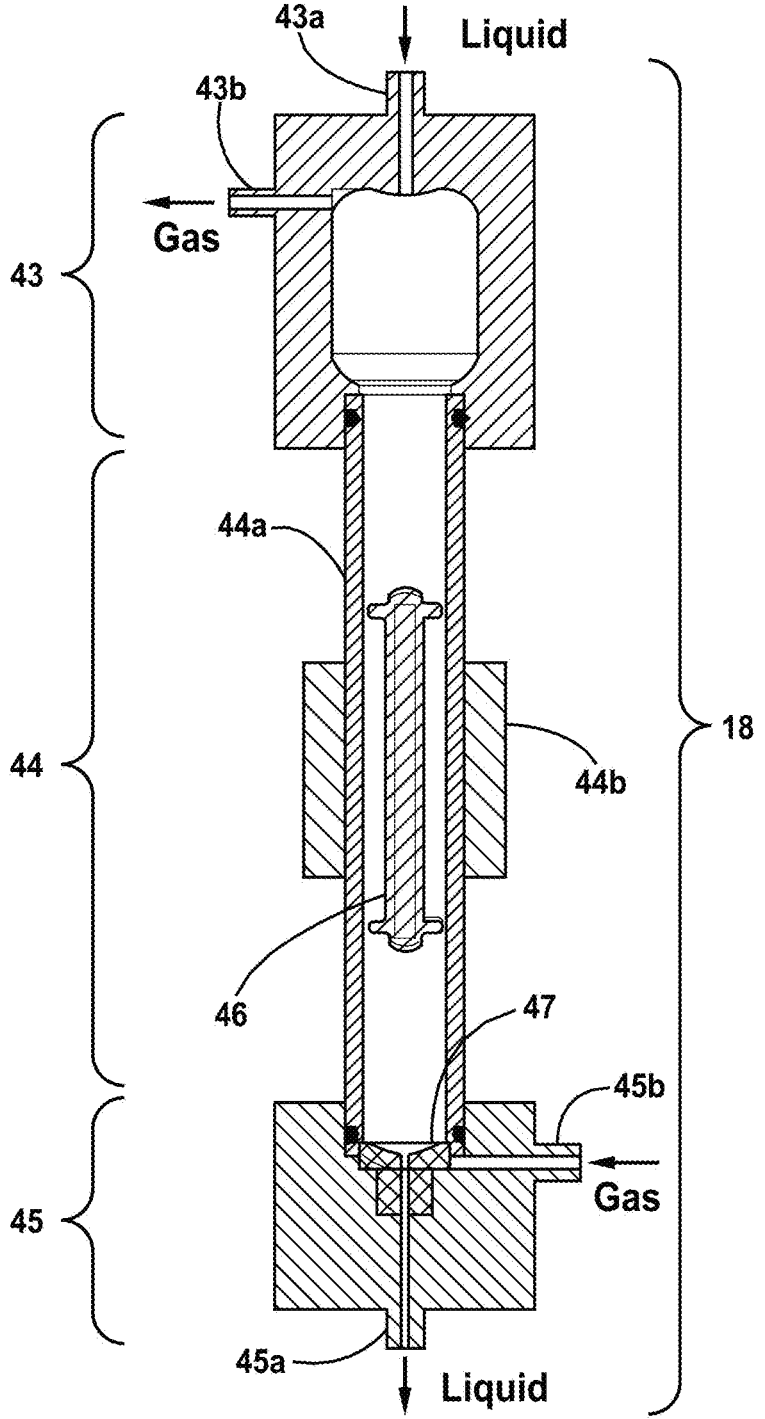
FIG. 3 (Sparger With Mixing Function) is a schematic, partially cut-away/sectional view of a mixer/sparger component.

One of the several components of embodiments of the apparatus described herein is the mixer/sparger 18. As shown in greater detail in FIG. 3, the mixer/sparger includes a liquid inlet/gas outlet section 43, a middle section 44, and a liquid outlet/gas inlet section 45. The top section 43 contains a liquid inlet 43a and the Sparge gas outlet 43b.

The bottom section 45 includes the inlet port 45b for the sparge gas and the outlet 45a for liquid. The middle section 44 includes a chamber element 44a located inside an annular solenoid coil 44b, which is activated by passing a series of current pulses through it. Such current waveform pulsing causes a magnetic stirrer 46 positioned inside chamber 44a to rapidly move up and down inside chamber 44a. In one embodiment, the magnetic stirrer 46 is coated with a corrosion-resistant outer layer, and its up-and-down action under the influence of the solenoid-generated waveform pulses causes the sample, reagents and dilution water, if any, inside chamber 44a to be rapidly mixed, typically in about 60 seconds or less. The bottom section 45 of mixer/sparger 18 includes a porous gas disperser 47, through which sparge gas is directed on its way into chamber 44a. The pore diameter in the gas disperser 47 may be about 1 µm to 0.125 in., e.g., preferably about 5 µm to 50 µm, and about 18 µm in one embodiment. The small bubbles produced by passing the sparge gas through disperser 47 results in efficient removal of IC from the liquid in chamber 44a, generally in about 10 seconds to 20 minutes at sparge gas flow rates ranging from about 50 to about 500 cc/min., typically and preferably in about one minute or less at a sparge gas flow rate of about 200 cc/min.

Figure 4:
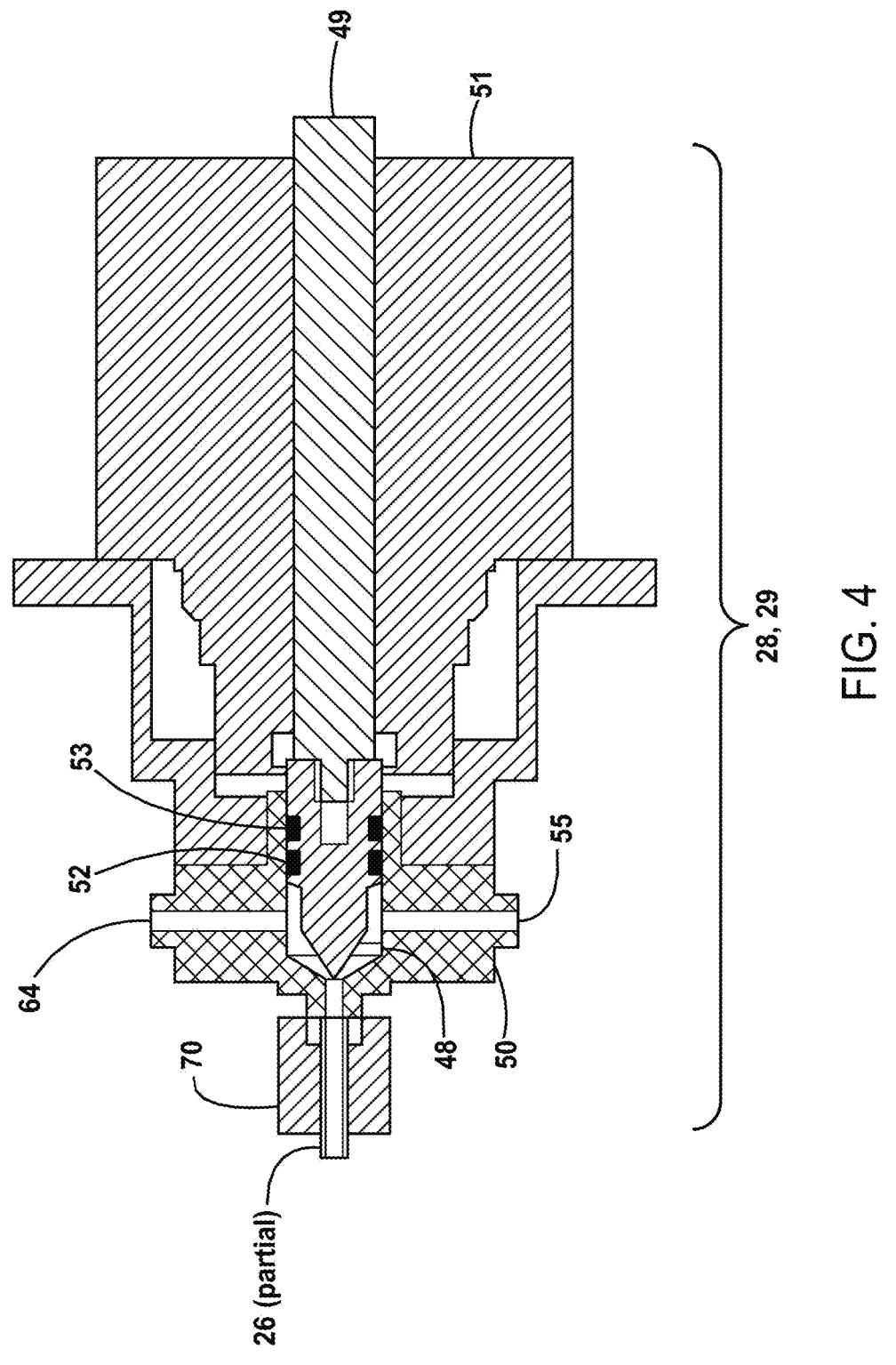
FIG. 4 (High-Pressure Valve) is a schematic, partially cut away/sectional view of a high-pressure reactor valve used to seal the reactor.

Another of the components of one of the embodiments of the apparatus are the high-pressure reactor valves 28 and 29 as shown in FIG. 2, and as illustrated in greater detail in FIG. 4. As seen in FIG. 4, a polymeric or elastic Seal 48 is attached to or comprises a front end or section of a moveable plunger element 49, which is designed to move back and forth inside the housing/valve body 50 when motor 51 is activated. The rear portion of seal 48 is adapted to retain first and second O-rings 52 and 53 respectively, which seal the interior of housing 50. The front end of seal 48 is sized and shaped to mate with and plug an opening (i.e., an inlet opening or an outlet opening) of reactor 26 when the valve is closed by advancing plunger element 49. Reactor 26 may be attached to valve housings 50, for example, using fittings 70 (as seen in FIG. 4), which provide a seal that is essentially leak-free at the pressure produced in reactor 26 when the solution/suspension is sealed inside reactor 26, and reactor 26 is heated.

Seal 48 is enclosed by a seal chamber defined by the valve housing 50 extending from the sealed opening of reactor 26 at least to first O-ring 52. This chamber can be continuously or periodically flushed with gas using seal chamber ports 54 and 55 as shown in FIG. 4. (Reactor valves 28 and 29 also each have a third port that is not seen in FIG. 4. The sample solution/suspension enters or exits the valve and the interior of reactor 26 through that third port.) This apparatus configuration makes it possible to remove any IC or free $CO_2$ that may be present in the valve housing 50 while the sample is being oxidized/treated in reactor 26.

Figure 5:
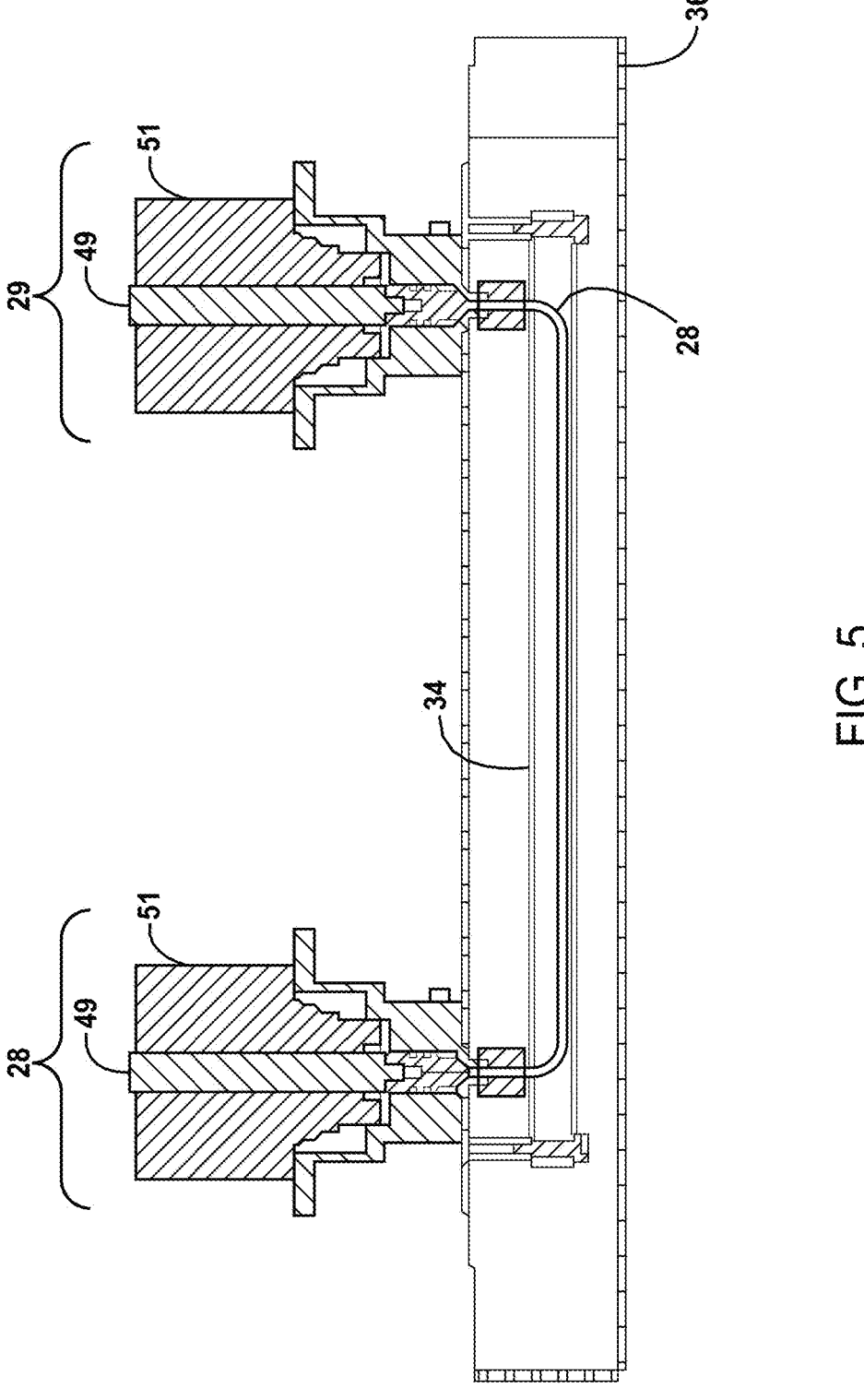
FIG. 5 (Reactor Assembly) is a schematic, partially cut away/sectional view of a reactor Sub-assembly.

FIG. 5 is a schematic illustration of reactor valves 28 and 29 mounted at either end of a reactor 26. In one embodiment, the reactor heater element 34 has a tubular configuration open at both ends and located inside a heater housing with the reactor 26 mounted inside the tubular portion of heater 34. In one embodiment, heater 34 comprises a thick-film heating element deposited on an electrically insulating coating on the tubular portion of heater 34, as shown in FIG. 5. The tubular portion of heater 34 may be constructed of stainless steel, titanium, or other suitable materials. The two ends of reactor 26 pass respectively through slots (not shown in FIG. 5) in the sidewall of the tubular portion of heater 34. In one embodiment, reactor 26 is a tube generally constructed of titanium; however, stainless steel, ceramics, and other materials that are sufficiently corrosion resistant and compatible with the oxidation temperatures required can be used including titanium and its alloys grade 7 and grade 7H, tantalum, Inconel 625, Hastelloy C-276, and the like. As previously discussed, the reactor assembly may also include a fan component to cool the reactor 26 after a heating/oxidation step. As seen in FIG. 5, the outlet (downstream side) of fan 36 may be positioned close to one open end of the heater 34, and is oriented so that a flow of cooling air during a cooling step passes through the heater housing and over both the exterior and interior of heater 34, and also such that the airflow going through the interior of the tubular portion of the heater 34 during a cooling step passes over the portion of reactor 26 contained within the tubular portion of heater 34.

An embodiment of the NDIR detector sub-assembly 5 is shown in greater detail in FIG. 6. The NDIR consists of an optical system and an associated NDIR electronic system (as illustrated in the block diagram of FIG. 7). The NDIR optical system generally has three sections: an IR source compartment 38, a sample cell/NDIR optical path 39, and an IR detector compartment 40. Collimating lenses 58 located at either end of sample cell 39 separate the adjacent sections. In one embodiment, the lenses 58 are constructed of silicon.

In one embodiment, the IR source 56 is a thin-film heater. It may be mounted in plates 59 that are attached to an IR source heater and an IR source temperature sensor. Using the associated NDIR electronic system, the plates 59 and IR source 56 are controlled to a temperature of about 65° C. in one embodiment.

In one embodiment, the IR detector 60 is a pyro electric, lithium tantalate sensor element. A 4.26 µm filter is mounted in the IR detector in front of the sensor element. This filter selectively passes infrared radiation at the wavelength that is absorbed by $CO_2$. Thus, the IR detector 60 measures the IR radiation that passes through the optical path 39 and the filter without being absorbed by $CO_2$.

The IR detector 60 may be mounted in plates 61 attached to an IR detector heater and an IR detector temperature sensor. In one embodiment, the IR detector 60 is controlled at a temperature of about 55° C. using the associated NDIR electronic system.

Carrier gas and the gas product from reactor 26, including the $CO_2$, flow through the center section 39 of the NDIR. IR source 56 and IR detector 60, located in their separate compartments, are isolated from water vapor and potentially corrosive oxidation products by the compartment separation lenses 58. The chambers 38 and 40 are also sealed, and $CO_2$ from ambient air is prevented from entering, or at least from remaining in, those chambers by flowing purge gas provided by the gas control sub-assembly 2. The center section 39 of the NDIR has a gas inlet port 62 and a gas outlet port 63, through which the carrier gas and the gas product from the reactor, including the $CO_2$, flow. As illustrated in FIG. 6, the gas inlet port 62 may be located proximate to the IR detector end of the NDIR, while the gas outlet port 63 is located proximate to the IR source end of the NDIR. However, the reverse orientation also is effective.

Figure 7:
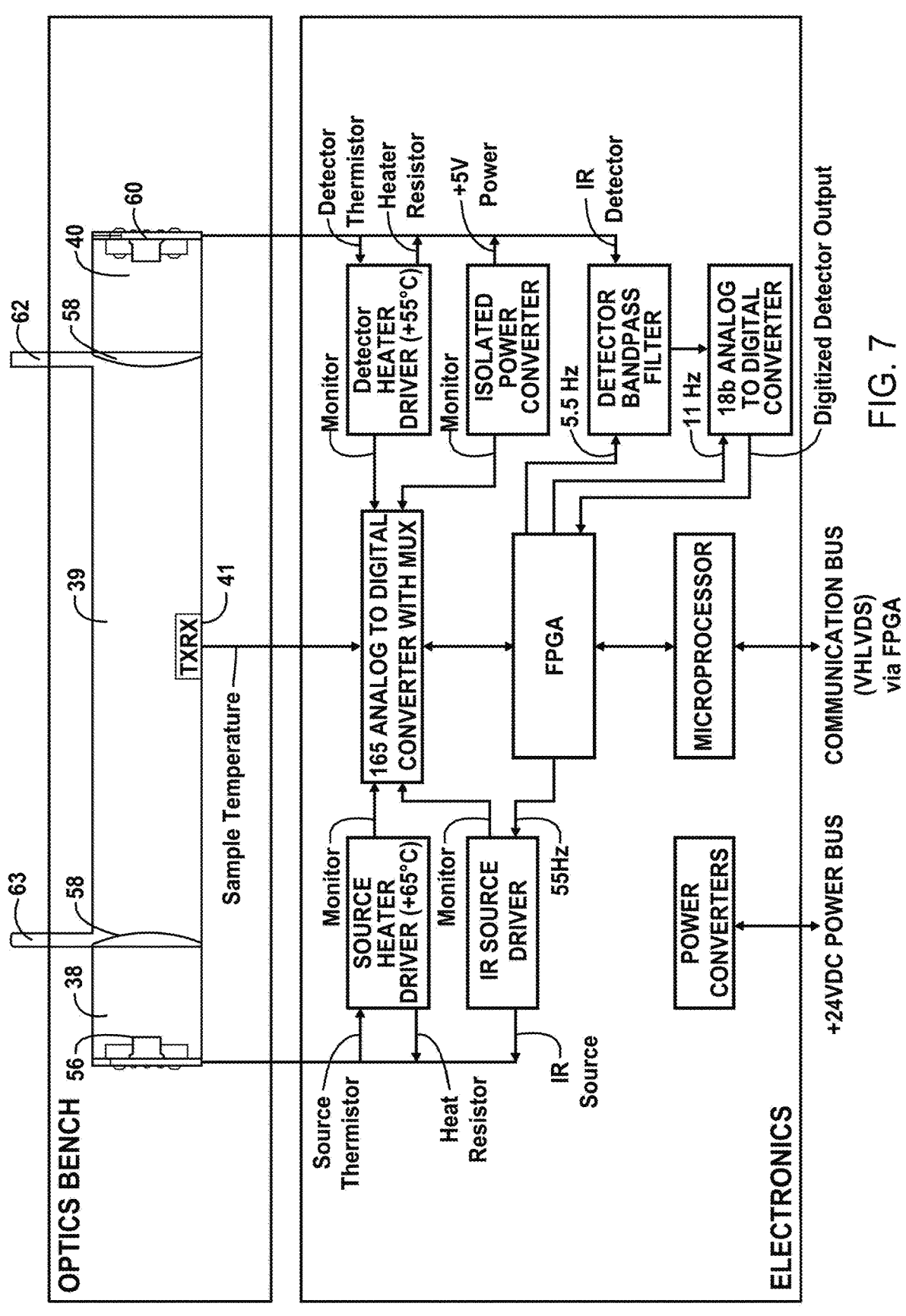
FIG. 7 (Block Diagram of NDIR Detector) is a block diagram illustrating internal details and related electrical connections and components of an NDIR sub-assembly as illustrated in FIG. 6.

The electronic system for operating the NDIR sub-assembly in one embodiment is schematically illustrated in FIG. 7. As seen in FIG. 7, the electronic system includes electronic devices selected to provide power to the IR source, the IR source heater, the IR detector, the IR detector heater, and other electrical components. In one embodiment, the electronics control system modulates the power to the IR source at a frequency of 55 Hz. Signals may be generated at other frequencies for operation of other components, such as the bandpass filter and analog-to-digital converter, from a field-programmable gate array (FPGA) as is known in the art.

The FPGA can be adapted or adjusted to generate a 55 Hz clock for the IR source, with a duty cycle suitable for its operation. The IR source driver converts the logic-level clock signal into the pulsed power required by the IR source. The IR source emits infrared light, modulated at 55 Hz. This light reaches the IR detector, attenuated by any $CO_2$ present in the center section 39 of the NDIR. The IR detector converts the infrared light that it receives back into an electrical signal, with signal content at 55 Hz that is proportional to the infrared light that it receives. The detector bandpass filter is selected or adapted to remove harmonics of the 55 Hz signal and DC offset, low-frequency noise, and high-frequency noise generated by the IR detector. A synchronous circuit, such as a Switched-capacitor filter, is used in the detector bandpass filter, with a clock provided by the FPGA at a multiple of 55 HZ. The analog-to-digital converter samples the waveform from the detector bandpass filter, also using a clock provided by the FPGA at a whole number multiple of 55 Hz. For example, a clock of 5500 HZ provides 100 waveform samples per cycle of the IR detector waveform. The FPGA and the microprocessor perform further bandpass filtering of the digitized IR detector signal, centered at the modulation frequency of 55 Hz, to remove detector noise and noise from the AC mains at 50 Hz or 60 Hz. The amplitude of the 55 Hz signal at the output of the digital bandpass filter is then measured. The response of the IR detector is adjusted for temperature, pressure, and flow rate as necessary, and the $CO_2$ concentration is calculated in the manner described above. Based on the description provided herein, the processing steps described above could readily be implemented by one of ordinary skill in this art using an apparatus in accordance with the described embodiments.

Figure 8:
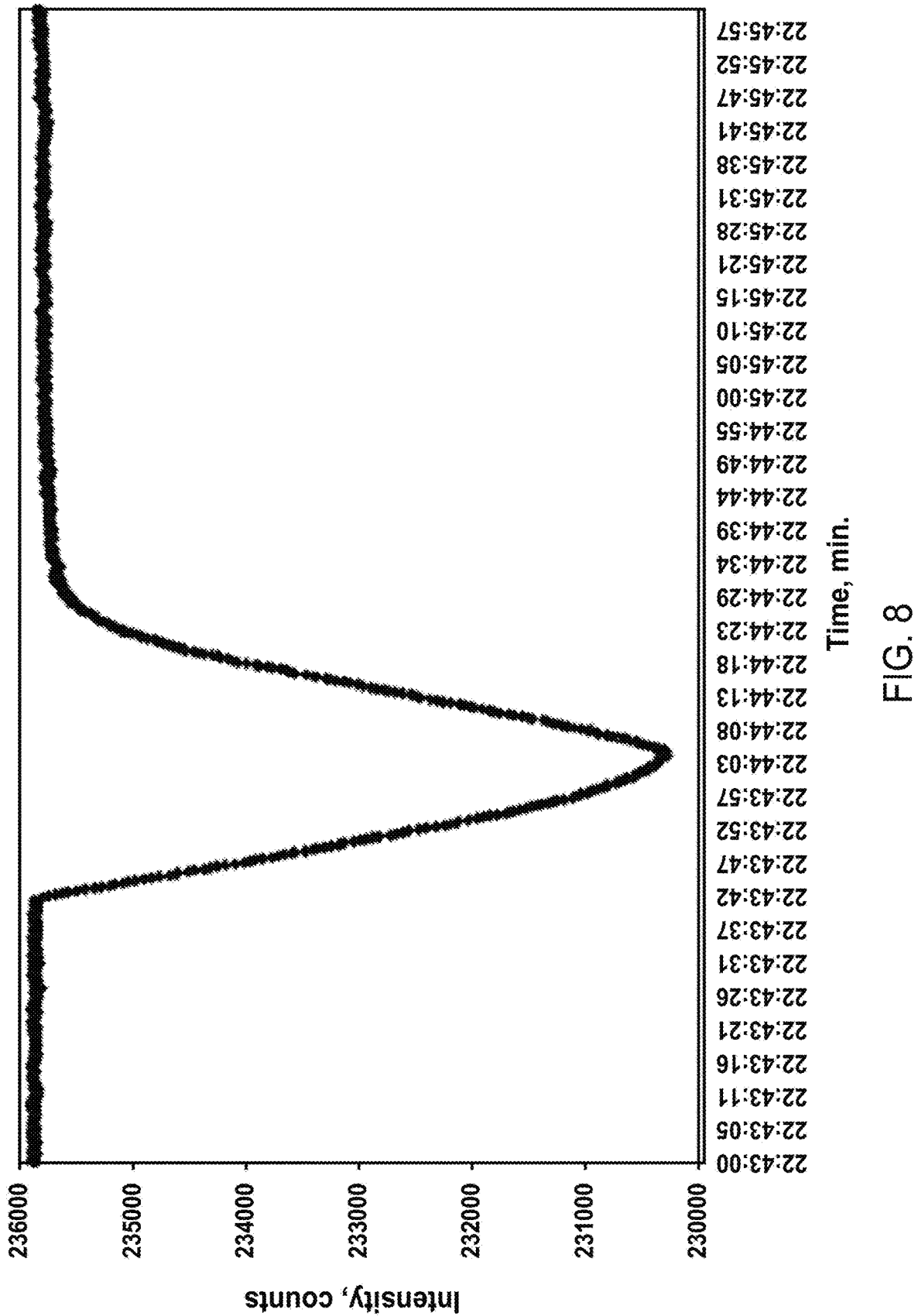
FIG. 8 (Response to $CO_2$) is a graph illustrating a typical response of a NDIR detector to $CO_2$ contained in a gaseous reactor product produced in the instrument by oxidation of organic compounds.

FIG. 8 illustrates a typical response curve of an NDIR during a carbon measurement sequence. The output is in instrument counts, and the counts are proportional to the amount of IR radiation that strikes the IR detector 60. When there is no $CO_2$ in section 39, the response is at its maximum or baseline level. As soon as $CO_2$ enters section 39, the response decreases until it reaches a minimum (trough) that 32 corresponds to when the amount of $CO_2$ in section 39 has reached its maximum (maximum absorbance). As the $CO_2$ passes out of section 39, the response returns to its original baseline level.

There are two ways that the response peak (trough) can be used to calculate carbon concentrations in an aqueous sample being tested. The response curve can be mathematically integrated, and the resulting cone-shaped area of the response curve can be related to carbon concentration by one type of mathematical calibration correlation. Alternatively, the height of the peak (depth of the trough) can be measured and related to carbon concentration by another type of mathematical calibration correlation. These mathematical calibration correlations can be developed for a particular instrument by performing tests on samples containing known concentrations of IC, OC and/or TC. Basing computations on the measurement of peak height has the advantage that it is relatively unaffected by changes in gas flow rate.

Figure 9:
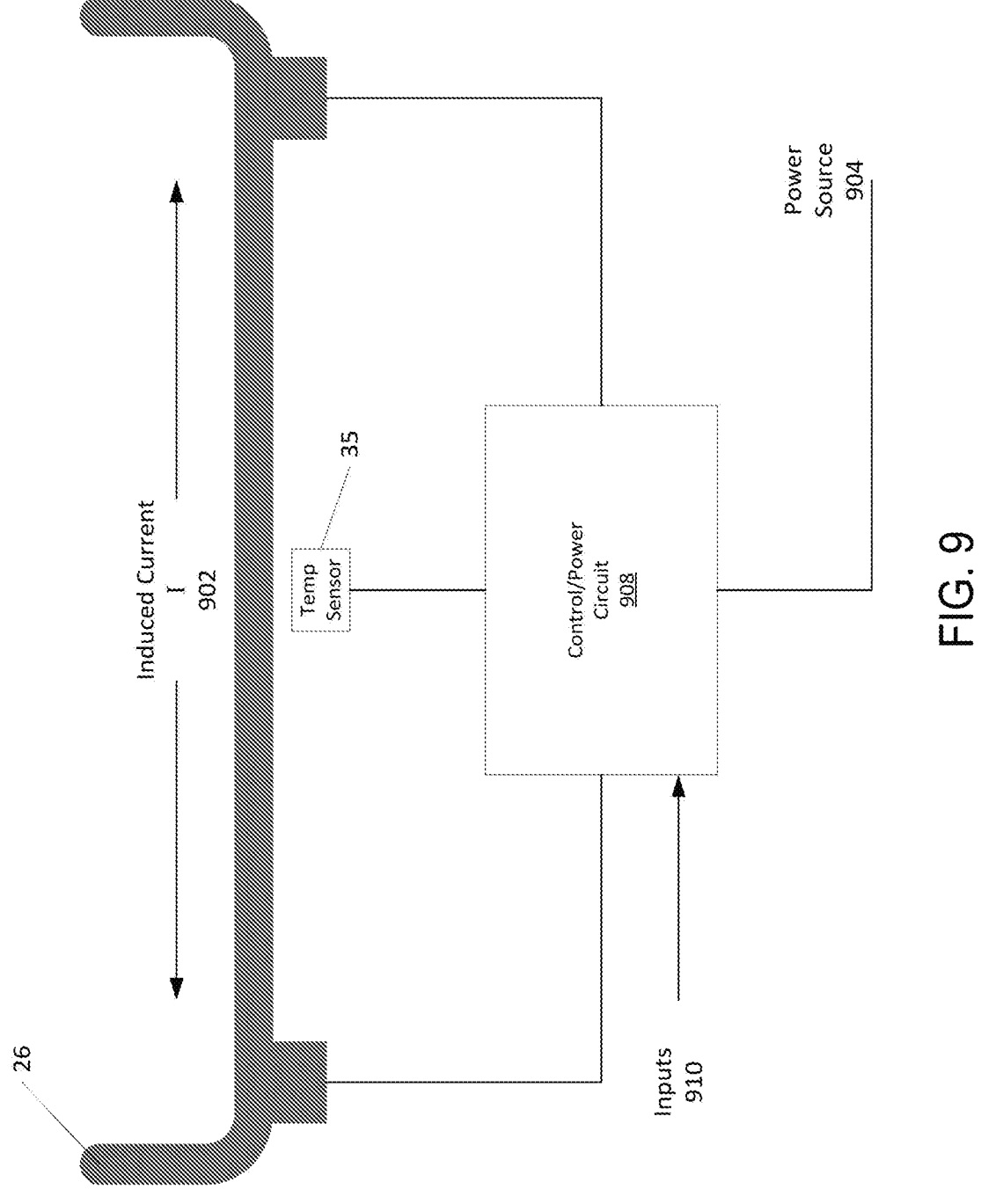
FIG. 9 is an illustration of a reactor of the measurement apparatus heated by passing an electric current through the material of the reactor.

In other embodiments, as shown in FIG. 9, the reactor 26 may be heated by the use of electrical current 902, passed directly through all or a portion of the reactor 26. Direct heating by electrical current may be used either in place of, or in addition to a heater 34 (as shown in FIG. 2). A power source 904 is used to pass the electrical current 902 through all or a portion of the reactor 206. The reactor material has a resistance R, that is inherent to the reactor material.

Electrical energy is dissipated as heat when an electrical current passes through reactor material. The heat dissipated can be characterized by the formula $P=I^2R$, where P is the power dissipated, I is the current flow through the material, and R is the resistance of the material the electrical current flows through. When the electrical current flows through the reactor, the resistance of the reactor material causes electrical energy to dissipate as heat. Therefore, passing an electrical current through the reactor 26 heats the reactor 26. The rate of heating is proportional to the resistance of the reactor and the square of the current passing through the reactor 26. As a result, no separate heater 34 or heating element is required to heat the reactor 26, and increased efficiency is possible.

To monitor and control the heating of the reactor 26 using an electrical current, sensing techniques as previously described may be applied. These include, but are not limited to, directly sensing the temperature of the reactor 26 using a temperature sensor 35 such as, for example, a RTD, detecting electromagnetic emissions produced by the reactor 26, and using an infrared (IR) sensor to measure the temperature of the reactor 26, and the like. Sensor 35 measurements produced may be used by a control circuit 908 to apply electrical current to the reactor 26, determine the magnitude or the applied current, and/or determine when to stop the flow of electrical current through the reactor 26. The control circuit 908 can use various inputs 910 to make these determinations in addition to sensed temperature of the reactor 26, including positions of valves, status of the measurement apparatus, and the like.

Figure 10:
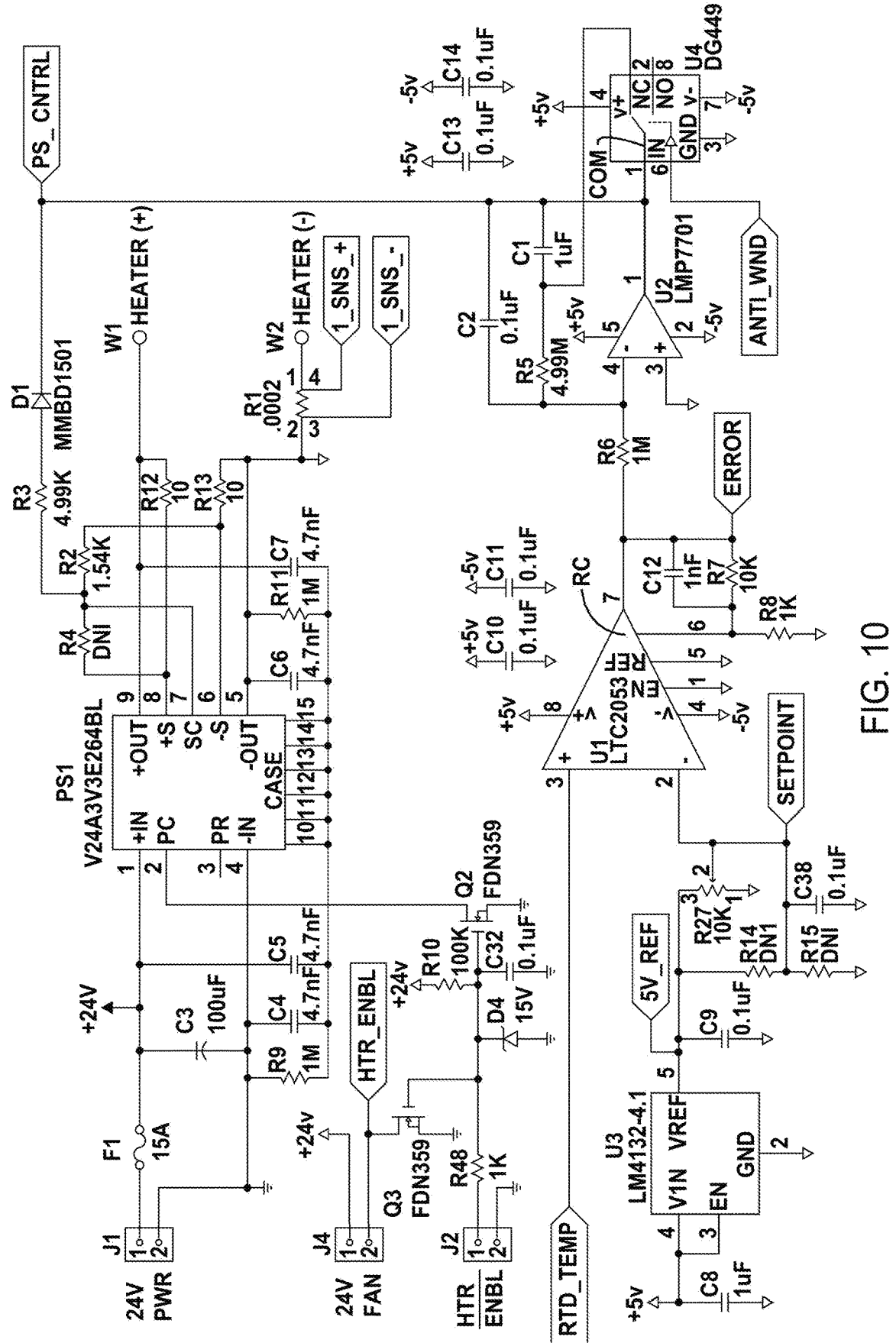
FIG. 10 is a schematic diagram detailing an exemplary circuit which may be used alone or in conjunction with other circuits to heat the reactor.

FIG. 10 illustrates a schematic diagram of either all or part of an exemplary circuit 908 for heating and controlling the reactor 26. FIG. 10 includes instrumentation amplifiers and DC converters configured to implement a reactor heating system.

Figure 11:
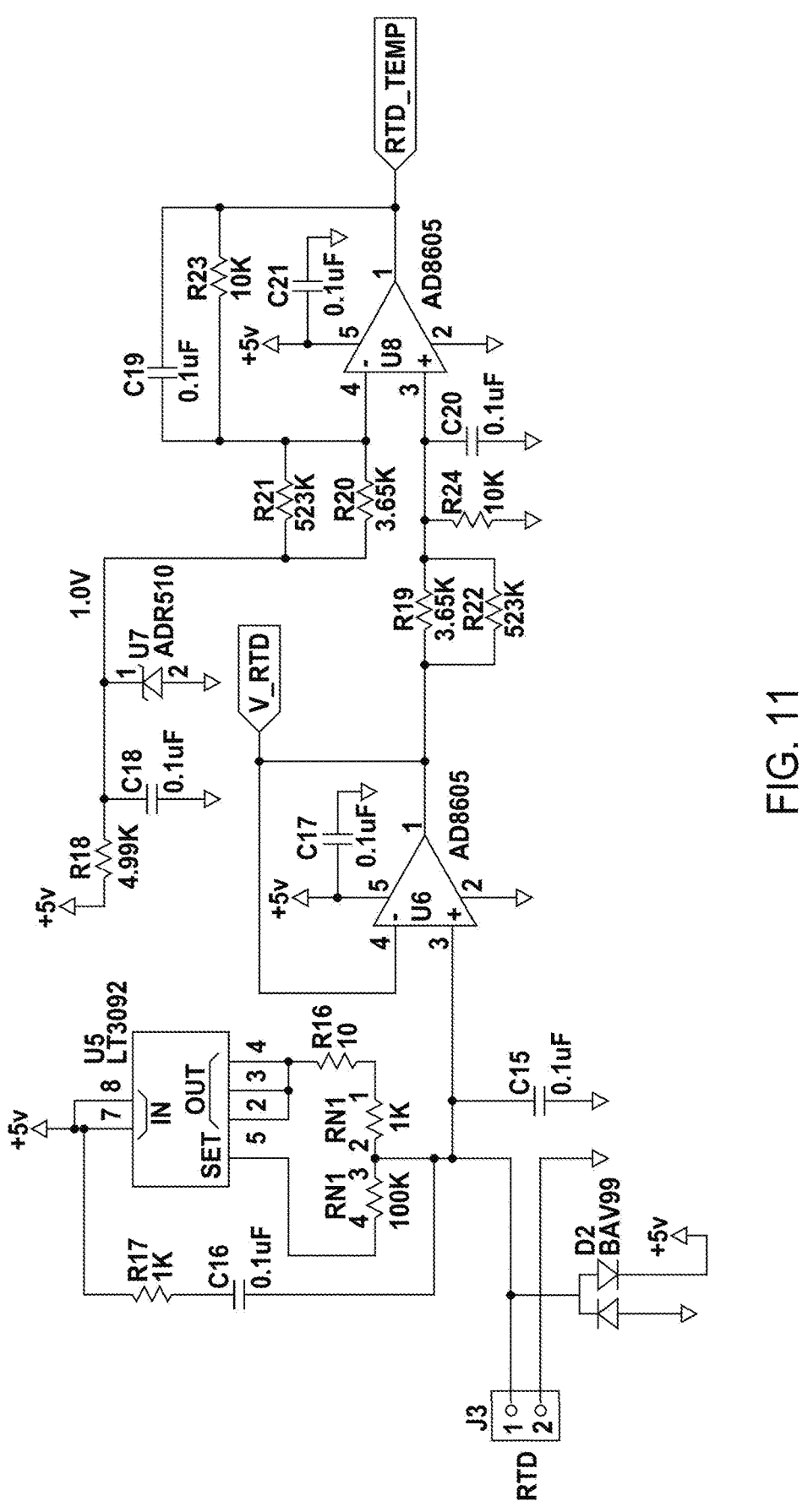
FIG. 11 is a schematic diagram detailing an exemplary circuit which may be used alone or in conjunction with other circuits to heat the reactor.
Figure 11:
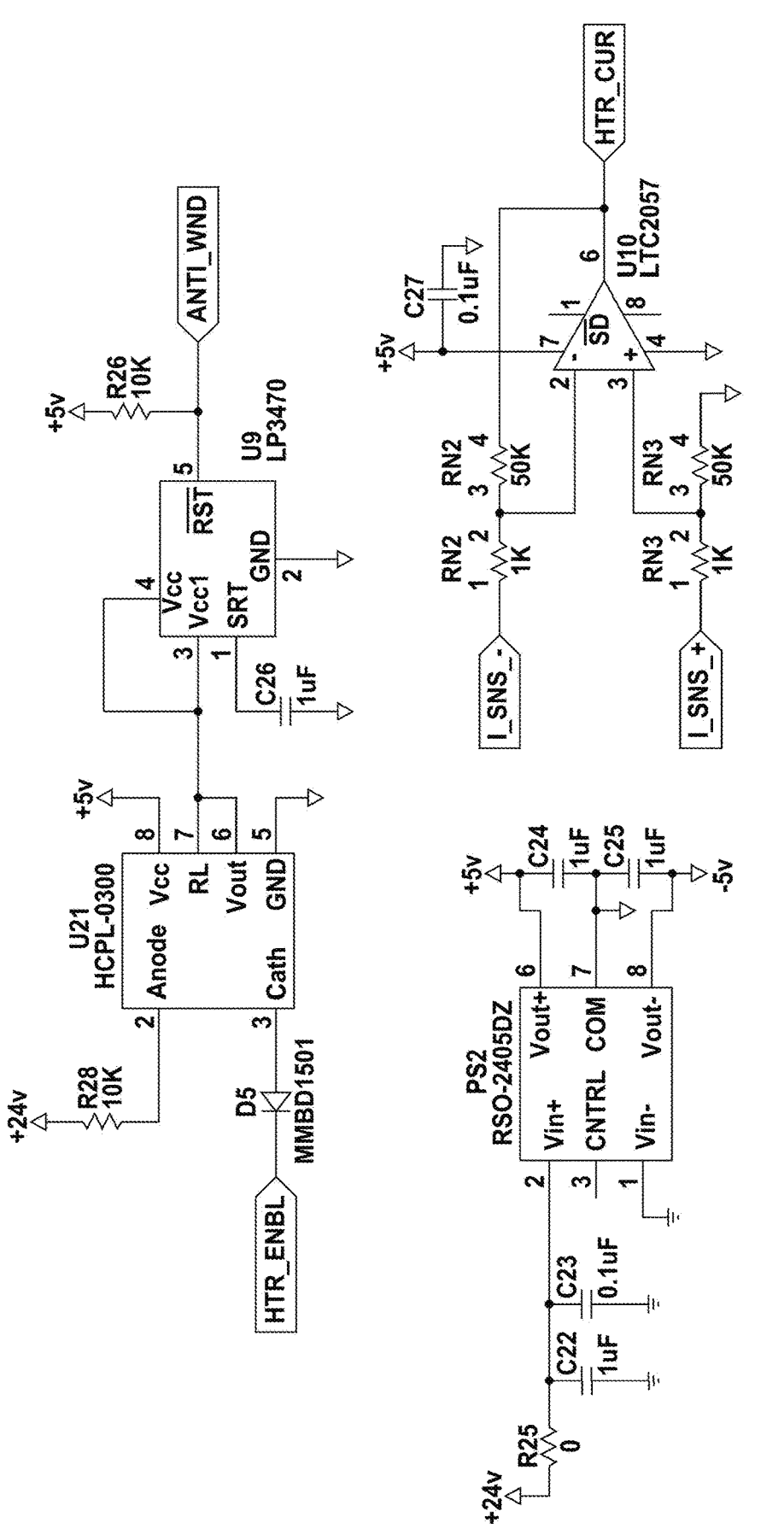

FIG. 11 also illustrates a schematic diagram of either all or part of an exemplary circuit 908 for heating and controlling the reactor 26. FIG. 11 includes amplifiers, and an optoisolator, configured to implement a reactor heating system.

Figure 12:
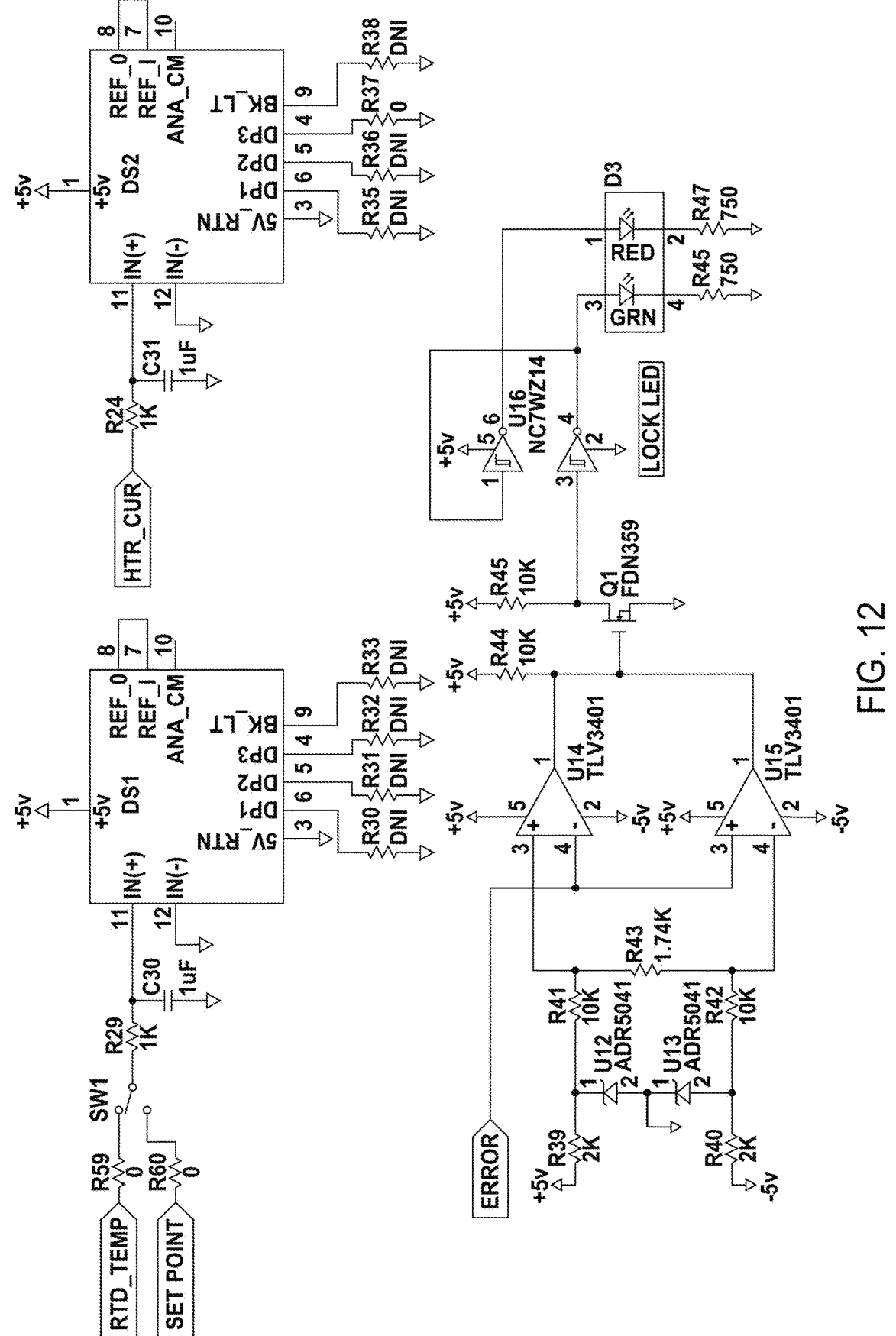
FIG. 12 is a schematic diagram detailing an exemplary circuit which may be used alone or in conjunction with other circuits to heat the reactor.
Figure 13:
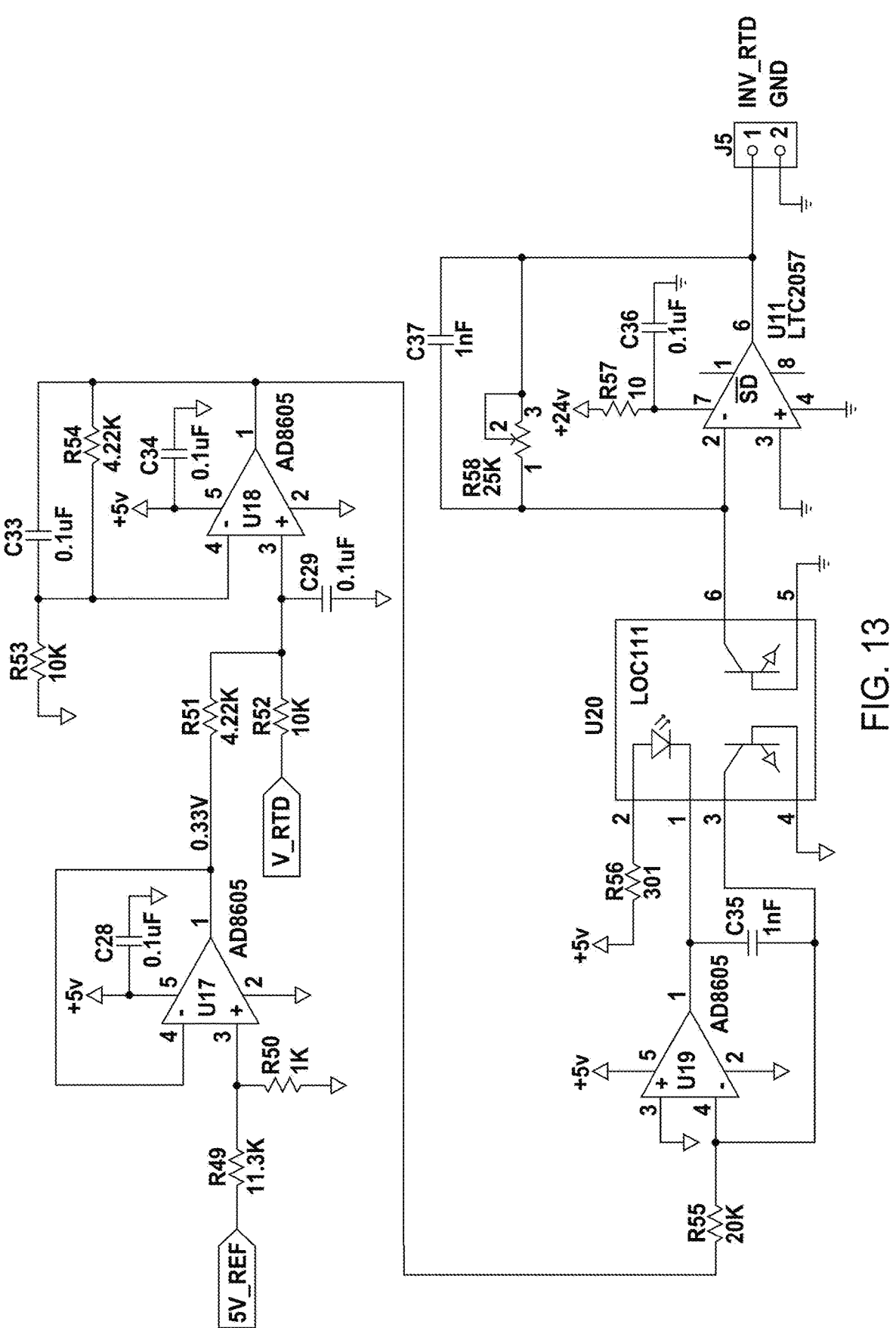
FIG. 13 is a schematic diagram detailing an exemplary circuit which may be used alone or in conjunction with other circuits to heat the reactor.

FIG. 12 also illustrates a schematic diagram of either all or part of an exemplary circuit 908 for heating and controlling the reactor 26. FIG. 12 includes a configuration of comparators used to implement an exemplary reactor heating circuit. Finally, FIG. 13 illustrates a schematic diagram of either all or part of an exemplary circuit 908 for heating and controlling the reactor. FIG. 13 includes a configuration of amplifiers used to implement an exemplary reactor heating circuit. The schematics disclosed in FIG. 10, FIG. 11, FIG. 12, and FIG. 13 are intended to be non-limiting examples, which may be applied separately or in various combinations.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications may be referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. An apparatus for treating a liquid sample containing organic material, said apparatus comprising:
  a reactor having reactor inlet and reactor outlet ports and a reactor interior for containing the liquid sample under above-ambient temperature and pressure conditions;
  high-pressure fluid reactor valve members at said reactor inlet and reactor outlet ports, said reactor valve members configured to allow a fluid to flow respectively into or out of the reactor interior when in an open-valve mode or, alternatively, configured to seal the reactor interior when in a closed-valve mode;
  a reactor heating system comprising an electrical current source operably connected to the reactor, the electrical current source configured to pass an electrical current through the reactor to rapidly and cyclically heat the reactor interior and the liquid sample sealed in the reactor interior to a temperature of about 150° C. to 650° C. or higher, while the reactor interior and the reactor valve members maintain the liquid sample under sealed conditions; and,
  a reactor cooling system adapted for rapidly and cyclically cooling the reactor interior and a reactor product sealed in the reactor interior following a heating cycle.

2. The apparatus of claim 1, wherein a sensor is configured to determine a temperature value of the reactor.

3. The apparatus of claim 2, wherein the sensor is configured to measure electromagnetic radiation.

4. The apparatus of claim 2, wherein the sensor is configured to measure infrared radiation.

5. The apparatus of claim 2, wherein the sensor is operably connected to the reactor heating system.

6. The apparatus of claim 2, wherein the sensor is operably connected to the reactor cooling system.

7. The apparatus of claim 2, wherein the reactor is comprised of titanium and its alloys, tantalum, Inconel 625, Hastelloy C-276, or combinations thereof.

8. A method for treating a liquid sample containing organic material utilizing a liquid sample treatment apparatus, the method comprising the steps of:
  providing a liquid sample treatment apparatus comprising the following features:
    a reactor having reactor inlet and reactor outlet ports and a reactor interior for containing the liquid sample under above-ambient temperature and pressure conditions;
    high-pressure fluid reactor valve members at said reactor inlet and reactor outlet ports, said reactor valve members configured to allow a fluid to flow respectively into or out of the reactor interior when in an open-valve mode or, alternatively, configured to seal the reactor interior when in a closed-valve mode;
    a reactor heating system comprising an electrical current source operably connected to the reactor, the electrical current source configured to pass an electrical current through the reactor to rapidly and cyclically heat the reactor interior and the liquid sample sealed in the reactor interior to a temperature of about 150° C. to 650° C. or higher, while the reactor interior and the reactor valve members maintain the liquid sample under sealed conditions; and
    a reactor cooling system adapted for rapidly and cyclically cooling the reactor interior and a reactor product sealed in the reactor interior following a heating cycle;
  mixing a known volume of the liquid sample with one or more other liquids selected from oxidizer, acid and dilution water to form a sample mixture;
  flowing at least a portion of the sample mixture into the interior of the reactor using the high-pressure fluid reactor valve members at said reactor inlet and reactor outlet ports, said reactor being adapted to be alternately and repeatedly opened and sealed at the reactor inlet and reactor outlet ports, said sample mixture containing the organic material;
  sealing the portion of sample mixture in the interior of the reactor by closing the valve members at the reactor inlet and reactor outlet ports;
  passing the electrical current through the reactor for a time sufficient substantially to heat and oxidize the organic material contained in the sample mixture and form the reactor product;
  stopping the heating step and then rapidly cooling the interior of the reactor and the reactor product inside to substantially ambient conditions to form cooled liquid and gaseous reactor products; and opening the reactor and removing the cooled liquid and gaseous reactor products form the reactor interior.

9. The method of claim 8, wherein the interior of the reactor and the sample portion inside is rapidly heated to a temperature between 150° C. to about 650° C.

10. The method of claim 8, wherein a sensor is provided, the sensor configured to measure a temperature value of the reactor.

11. The method of claim 10, wherein the sensor is configured to measure electromagnetic radiation.

12. The method of claim 10, wherein the sensor is configured to measure infrared radiation.

13. The method of claim 10, wherein a signal generated by the sensor is used to decide when to stop the heating step.

14. The method of claim 8, wherein the reactor is comprised of titanium and its alloys, tantalum, Inconel 625, Hastelloy C-276, or combinations thereof.

\* \* \* \* \*